US006203507B1

(12) United States Patent
Wadsworth et al.

(10) Patent No.: US 6,203,507 B1
(45) Date of Patent: Mar. 20, 2001

(54) DEFLECTABLE CATHETER WITH ERGONOMIC HANDLE

(75) Inventors: John F. Wadsworth, Los Angeles; J. Kevin Clay, Oxnard; Stanley H. Wada, Tarzana; Edward V. Cruz, Newbury Park, all of CA (US)

(73) Assignee: Cordis Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/262,136

(22) Filed: Mar. 3, 1999

(51) Int. Cl.[7] .............................. A61B 5/00
(52) U.S. Cl. .............................. 600/585
(58) Field of Search .............................. 600/585, 433, 600/434; 604/95, 96, 280, 281

(56) References Cited

U.S. PATENT DOCUMENTS

| | | | | |
|---|---|---|---|---|
| Re. 34,502 | | 1/1994 | Webster, Jr. | 607/125 |
| 3,416,531 | | 12/1968 | Edwards | 128/348 |
| 3,552,384 | | 1/1971 | Pierie et al. | 128/2.05 |
| 3,847,140 | | 11/1974 | Ayella | 128/2 M |
| 4,886,067 | * | 12/1989 | Palermo | 600/585 |
| 4,960,134 | | 10/1990 | Webster, Jr. | 128/786 |
| 5,125,896 | | 6/1992 | Hojeibane | 604/95 |
| 5,170,787 | | 12/1992 | Lindegren | 128/642 |
| 5,190,050 | * | 3/1993 | Nitzsche | 600/585 |
| 5,242,441 | | 9/1993 | Avitall | 606/41 |
| 5,287,858 | * | 2/1994 | Hammerslag et al. | 600/585 |
| 5,327,905 | * | 7/1994 | Avitall | 600/585 |
| 5,368,564 | | 11/1994 | Savage | 604/95 |
| 5,383,923 | | 1/1995 | Webster, Jr. | 607/125 |
| 5,431,168 | | 7/1995 | Webster, Jr. | 128/658 |
| 5,465,716 | | 11/1995 | Avitall | 128/642 |
| 5,489,270 | | 2/1996 | van Erp | 604/95 |
| 5,562,619 | | 10/1996 | Mirarchi et al. | 604/95 |
| 5,656,030 | | 8/1997 | Hunjan et al. | 604/95 |
| 5,662,606 | | 9/1997 | Cimino et al. | 604/95 |

FOREIGN PATENT DOCUMENTS

WO 97/28839 8/1997 (WO) .

* cited by examiner

*Primary Examiner*—Max Hindenburg
*Assistant Examiner*—Panela Wingood
(74) *Attorney, Agent, or Firm*—Christie, Parker & Hale, LLP

(57) ABSTRACT

A deflectable catheter comprises a catheter body, a tip section and a control handle. The Control handle, which is preferably curved, comprises a housing having a generally hollow interior, a piston receiving assembly at least partially within the interior of the housing, and a piston. The piston receiving assembly is afforded rotational movement but not longitudinal movement relative to the housing and comprises a generally tubular member defining a piston chamber. The piston is fixedly attached to the proximal end of the catheter body and extends into the piston chamber of the piston receiving assembly, wherein the piston is afforded longitudinal movement but not rotational movement relative to the piston receiving assembly. Rotation of the piston relative to the housing correspondingly rotates the piston receiving assembly, catheter body and tip section. A puller wire extends from the control handle, through a lumen in the catheter body and into a lumen in the tip section. The proximal end of the puller wire is anchored in the control handle, whereby distal movement of the piston relative to the piston receiving assembly results in distal movement of the catheter body relative to the puller wire. The puller wire is anchored in the tip section so that to distal movement of the catheter body relative to the puller wire deflects the tip section.

18 Claims, 7 Drawing Sheets

DEFLECTABLE CATHETER WITH ERGONOMIC HANDLE

FIELD OF THE INVENTION

The present invention relates to a deflectable catheter having an ergonomic control handle.

BACKGROUND OF THE INVENTION

Electrode catheters have been in common use in medical practice for many years. They are used to stimulate and map electrical activity in the heart and to ablate sites of aberrant electrical activity. In use, an electrode catheter is inserted into a major vein or artery, e.g., femoral artery, and then guided into the chamber of the heart which is of concern. The catheter should preferably be deflectable to permit proper positioning of the electrodes on its distal end within the heart.

Deflectable tip electrode catheters are well known. Such a catheter generally has a control handle at its proximal end for controlling deflection of the tip in one or more directions. For example, a particularly useful deflectable tip catheter is disclosed in U.S. Pat. No. Re. 34,502 to Webster, the disclosure of which is hereby incorporated by reference. This catheter comprises a puller wire that extends on-axis through an elongated reinforced catheter body and then off-axis in a deflectable tip portion. In this arrangement, longitudinal movement of the puller wire relative to the catheter body results in deflection of the catheter tip portion. Other examples of steerable catheters can be found in U.S. Pat. No. 5,431,168 to Webster entitled “Steerable Open-Lumen Catheter” and U.S. patent application Ser. No. 08/924,611 to Webster entitled “Omni-Directional Steerable Catheter,” the disclosures of which are hereby incorporated by reference.

A consideration when designing a deflectable catheter is the comfort to the user. In particular, the handle should be comfortable to hold and easy to manipulate when rotating and deflecting the tip section.

SUMMARY OF THE INVENTION

The present invention provides a deflectable tip catheter having a comfortable, ergonomic handle. In one embodiment, the deflectable tip catheter comprises a catheter body, a tip section, and an ergonomic control handle. The catheter body has proximal and distal ends and at least one lumen extending therethrough. The tip section similarly comprises proximal and distal ends and at least one lumen extending therethrough. The proximal end of the tip section is fixedly attached to the distal end of the catheter body.

The control handle comprises a housing having a generally hollow interior, a piston receiving assembly at least partially within the interior of the housing, and a piston. The piston receiving assembly is afforded rotational movement relative to the housing. The piston receiving assembly comprises a generally tubular member defining a piston chamber. The piston is fixedly attached to the proximal end of the catheter body and extends into the piston chamber of the piston receiving assembly. The piston is afforded longitudinal movement relative to the piston receiving assembly but is not afforded rotational movement relative to the piston receiving assembly. Accordingly, rotation of the piston relative to the housing correspondingly rotates the piston receiving assembly, catheter body and tip section. By this design, the user can hold the handle in a stationary position and rotate the catheter body and tip section by merely rotating the piston. Previous designs, e.g., as discussed in U.S. Pat. No. Re 34,502, required that the user rotate the entire handle, include the housing, to rotate the catheter body and tip section.

To deflect the tip section, a puller wire having proximal and distal ends extends from the control handle, through a lumen in the catheter body and into a lumen in the tip section. The proximal end of the puller wire is anchored in the control handle, preferably in the piston receiving assembly, so that distal movement of the piston relative to the piston receiving assembly results in distal movement of the catheter body relative to the puller wire. Means are provided for deflecting the tip section in response to distal movement of the catheter body relative to the puller wire. A preferred deflecting means comprises an off-axis lumen in the tip section into which the puller wire extends and an anchor that anchors the puller wire to the tip section. Another deflecting means is described in U.S. Pat. Nos. 5,336,182 and 5,364,351, the disclosures of which are incorporated herein by reference.

In a particularly preferred embodiment, the handle housing comprises a generally cylindrical distal portion and a curved proximal portion for gripping. To permit the user to hold the handle in a stationary position while rotating the catheter body and tip section, a novel piston receiving assembly is provided. The piston receiving assembly comprises a rigid tubular distal barrel and means for carrying electrode lead wires, a sensor cable and thermocouple wires from the distal barrel to a connecter at the proximal end of the handle. The distal barrel, which lies within the handle housing, is generally tubular at its distal end, forming a piston chamber therein. A preferred carrying means comprises a rigid proximal barrel connected to the distal barrel, preferably by a universal coupling. The proximal barrel, which is contained at least in part within the handle housing, is generally tubular. By means of the universal coupling, rotation of the distal barrel results in corresponding rotation of the proximal barrel.

A particularly preferred deflectable catheter comprises a tip section having varying stiffness. The tip section comprises a flexible tubing having proximal and distal ends and at least two lumens extending therethrough. The flexible tubing has at least two different stiffnesses, and preferably three to five different stiffnesses, along its length. In a particularly preferred embodiment, the flexible tubing comprises a plastic core, a metal braid over the core, a plastic skin over the braid, and at least two, and preferably three to five, pieces of plastic tubing in longitudinal arrangement extruded over the plastic skin. The pieces of plastic tubing have different stiffnesses and are arranged with the stiffer tubing being proximal the less stiff tubing.

A preferred method for making a catheter tip section of varying stiffness comprises extruding a plastic core over at least two, and preferably three, mandrels, thereby forming lumens. Preferably metal is braided over the plastic core. Thereafter, at least two, and preferably three to five, pieces of plastic tubing having different degrees of stiffness are assembly along the length of the plastic core so that the piece of plastic tubing having the greatest stiffness is at the proximal end of the tip section and the piece of plastic having the lowest stiffness is near the distal end of the tip section. The pieces of plastic tubing are then melted to bond with the plastic core.

A particularly preferred method comprises first extruding a plastic core over at least two mandrels. Metal is braided over the plastic core. Thereafter, a thin skin of plastic is extruded over the metal braid to form an inner core. At least two, and preferably three to five, pieces of plastic tubing having different degrees of stiffness are assembled in surrounding relation to the inner core to form an assembly where the piece of plastic tubing having the greatest stiffness is at the proximal end of the assembly and the piece of plastic having the lowest stiffness is near the distal end of the assembly. A shrink sleeve is placed over the entire assembly. The pieces of plastic tubing are then heated sufficiently to bond them to the inner core, and the shrink sleeve is then removed.

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
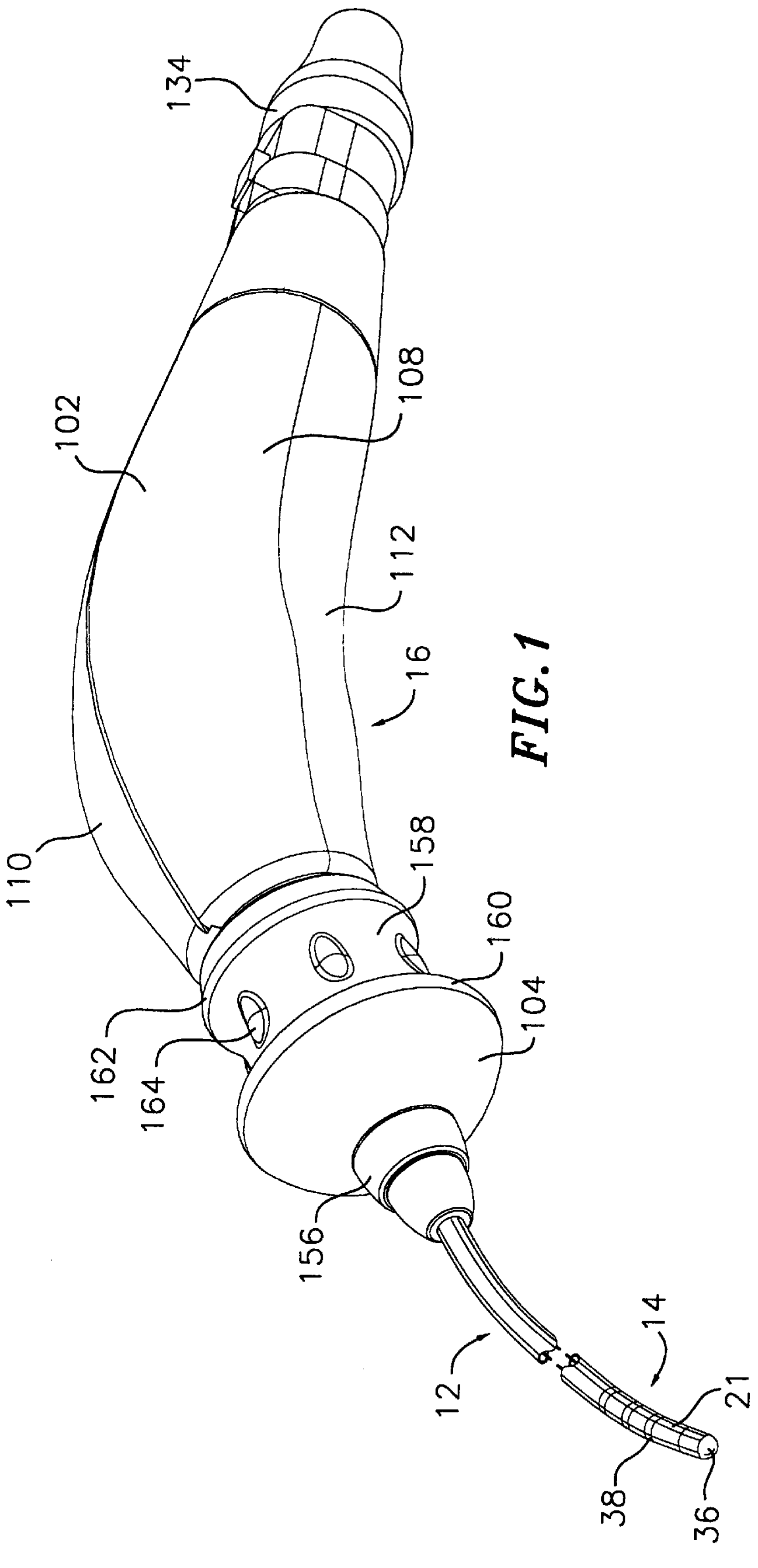
FIG. 1 is a side cross-sectional view of an embodiment of the catheter of the invention.

In a particularly preferred embodiment of the invention, there is provided a deflectable catheter. As shown in FIG. 1, the catheter comprises an elongated catheter body 12 having proximal and distal ends, a tip section 14 at the distal end of the catheter body 12, and a control handle 16 at the proximal end of the catheter body 12.

Figure 2:
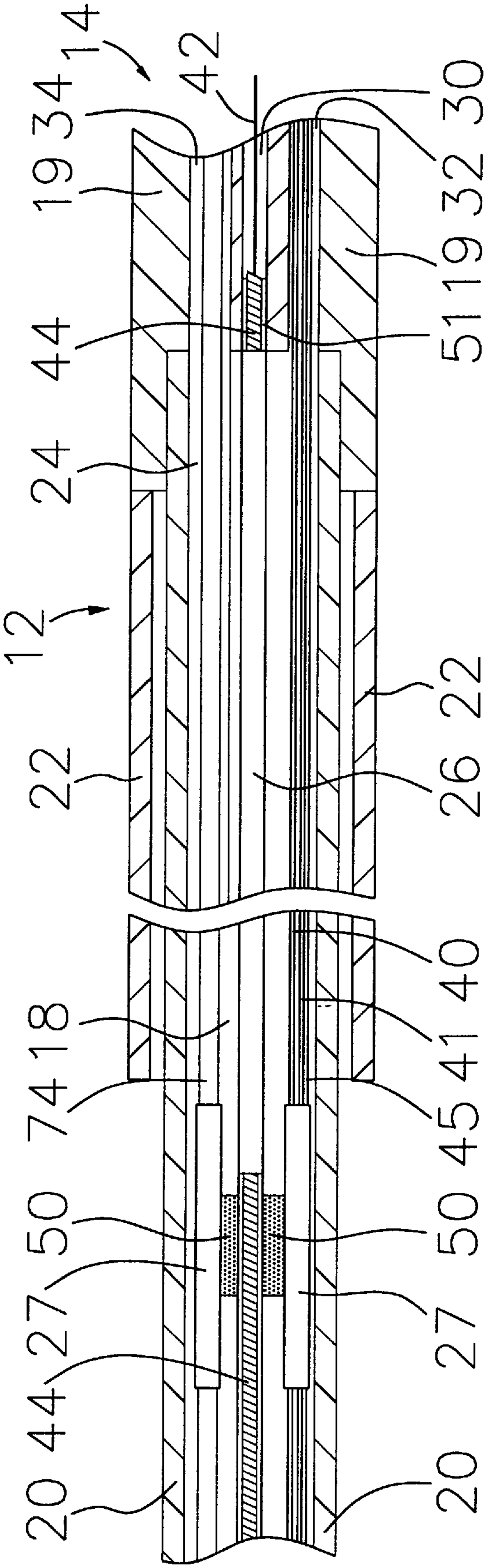
FIG. 2 is a side cross-sectional view of the catheter body, including the junction between the catheter body and the tip section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 french, more preferably no greater than about 7 french. Likewise the thickness of the outer wall 22 is not critical. The inner surface of the outer wall 22 is lined with a stiffening tube 20, which can be made of any suitable material that is more flexible than the outer wall 22, preferably polyimide. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred because it may be very thin-walled while still providing very good stiffness. This maximizes the diameter of the central lumen 18 without sacrificing strength and stiffness.

A particularly preferred catheter has an outer wall 22 with an outer diameter of from about 0.090 inch to about 0.094 inch and an inner diameter of from about 0.061 inch to about 0.65 inch and a polyimide stiffening tube 20 having an outer diameter of from about 0.0595 inch to about 0.635 inch and an inner diameter of about from about 0.049 inch to about 0.055 inch.

Figures 3A, 3B:
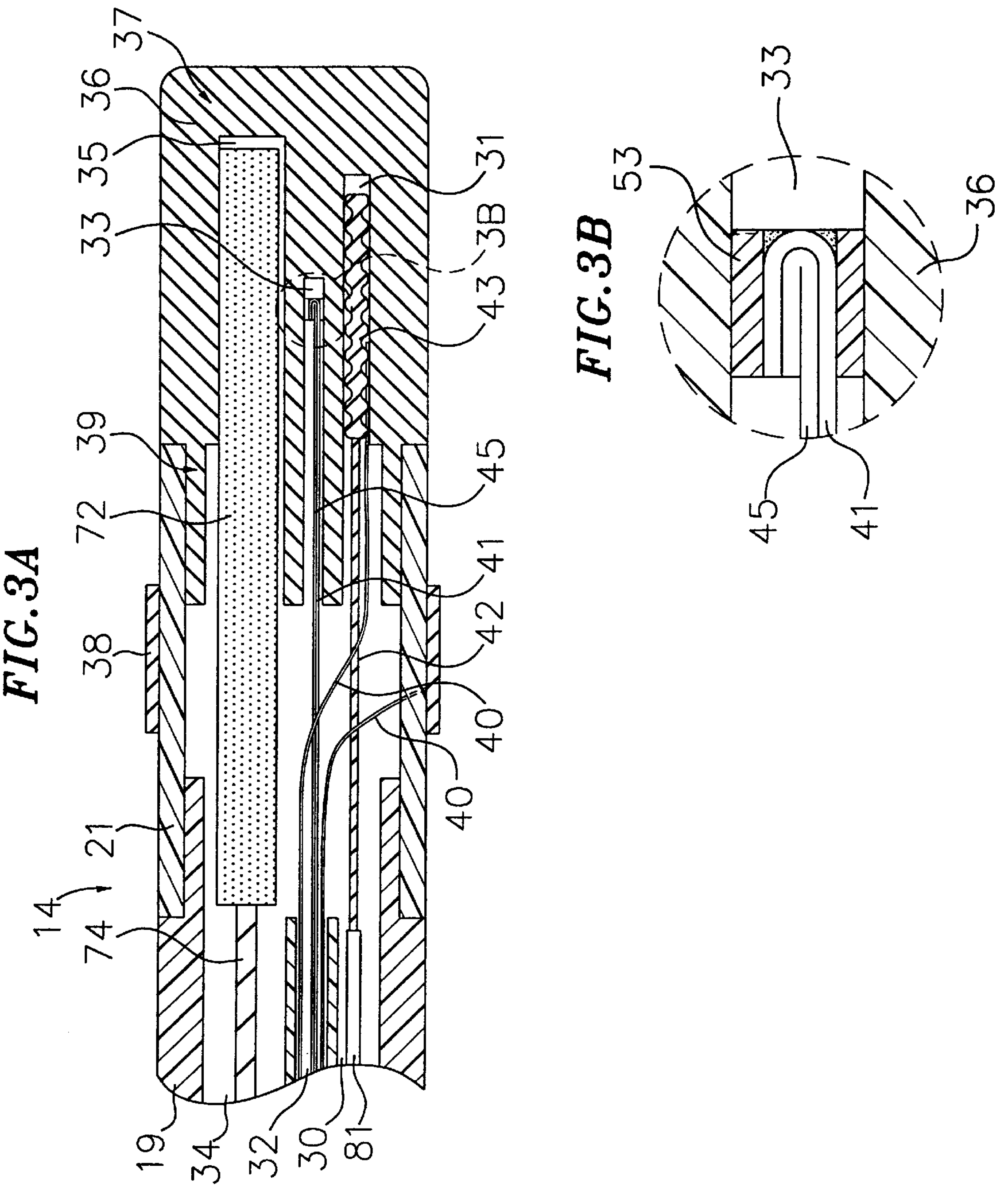
FIG. 3A is a side cross-sectional view of the catheter tip section.
FIG. 3B is an enlarged view of the thermocouple anchored within the tip electrode illustrated in FIG. 3A.
Figure 4:
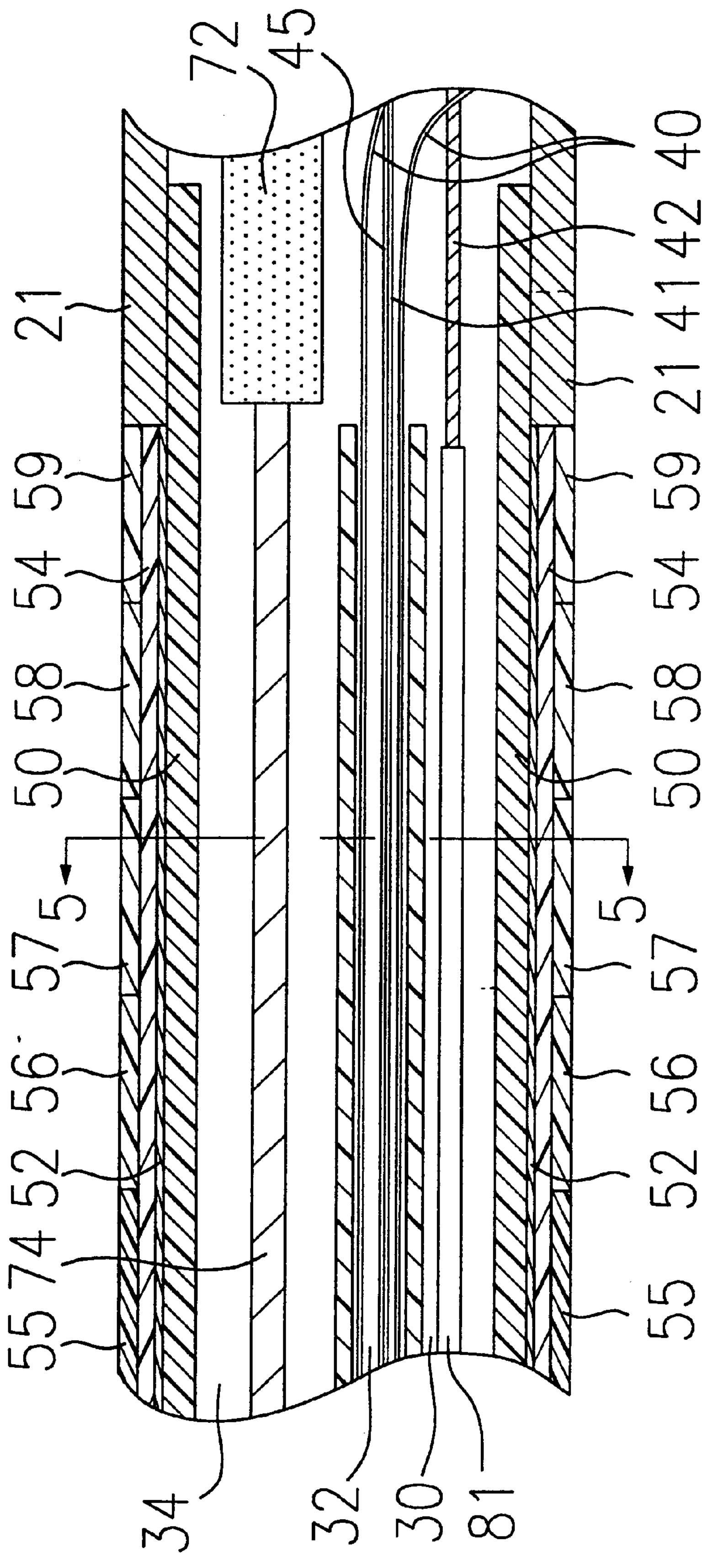
FIG. 4 is a side cross-sectional view of a portion of the catheter tip section showing the structure of the flexible tubing.
Figure 5:
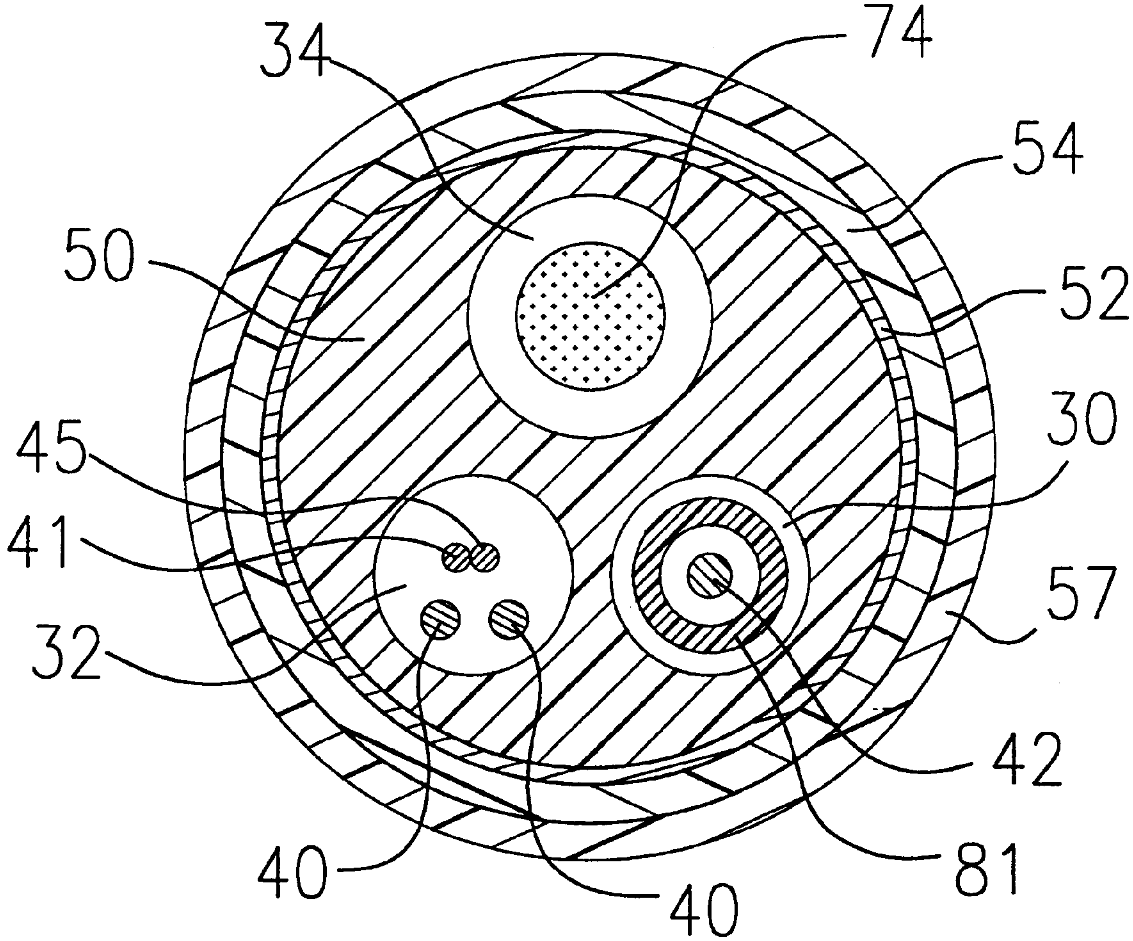
FIG. 5 is a transverse cross-sectional view of the catheter tip section of FIG. 4 along line 5—5.

As shown in FIGS. 3 to 5, the tip section 14 comprises a short section of flexible tubing 19 having three lumens, a first lumen 30, a second lumen 32, and a third lumen 34. The tubing 19 is made of a suitable non-toxic material that is preferably more flexible than the catheter body 12. A presently preferred tip section 14 has varying stiffness along its length, with the distal end being the most flexible and the proximal end being the least flexible. Preferably the tip section 14 has at least two different stiffnesses along its length, more preferably at least three, still more preferably at least five. By varying the stiffness along the length of the tip section, the distal end of the tip section can be made to be extremely soft, while the proximal end of the tip section can have a stiffness more similar to that of the catheter body. The soft tip section is desirable because it is safer when the tip section is being passed through the body. However, if the entire tip section is extremely soft, then it is floppy and difficult to maneuver. Thus, by having a relatively less flexible proximal end, the tip section is easier to maneuver in use.

To manufacture a particularly preferred tip section having varying stiffness a core 50, preferably a 0.71 inch 65D polyurethane core, is extruded over three mandrels. The mandrels are preferably Teflon coated wires. The diameters of the wires will depend on the desired sizes of the lumens. In a particularly preferred embodiment, two of the wires have a 0.022 inch diameter and the third has a 0.036 inch diameter. A braided stainless steel mesh 52 is provided over the polyurethane core. In a preferred embodiment, 0.002 inch stainless steel wire (45 picks) with sixteen strands per carrier is braided over the core. A thin skin 54 of polyurethane or other suitable plastic is then extruded over the braid 52 to form an inner core. The inner core is then cut into 5 inch segments with the mandrels still inside. As would be recognized to one skilled in the art, the length of the segment can vary depending on the desired overall length of the tip section. Five pieces of plastic, preferably polyurethane, tubing are assembled over the inner core. Each of the five pieces has a different stiffness. In a preferred embodiment, the plastic pieces include 75D polyurethane tubing 55, 65D polyurethane tubing 56, 55D polyurethane tubing 57, 80/20% polyurethane tubing 58, and 80A polyurethane tubing 59. The 75D polyurethane tubing 55 is used to form the proximal end of the tip section, and the 80A polyurethane tubing 59 is used to form the distal end of the tip section. A shrink sleeve, preferably made of Teflon™ is placed over the entire assembly. The assembly is pulled through a hot die, and the pieces of polyurethane tubing are melted to the inner core. The shrink sleeve is removed, and the wire mandrels are removed. The resulting tip section has three lumens and five different stiffness along its length. Preferably the outer diameter of the tip section 14, like that of the catheter body 12, is preferably no greater than about 8 french, more preferably no greater than about 7 french (0.092 inch). This method is particularly useful for tip sections having at least two, and preferably three or more, lumens extending therethrough.

At the distal end of the tip section 14 is a tip electrode 36. Preferably the tip electrode 36 has a diameter about the same as the outer diameter of the tubing 19. A preferred tip electrode 36 has an exposed section 37 having a length of about 2 mm and a stem 39, having a diameter less than the diameter of the exposed section and having a length of about 2 mm. The stem 39 and exposed section 37 of the tip electrode 36 are generally solid, having 3 blind holes 31, 33 and 35 extending from the proximal end of the stem 39 part way into the exposed section 37.

The tip electrode 36 is connected to the tubing 19 by means of a generally rigid tubular plastic housing 21, preferably made of polyetheretherketone (PEEK). The stem 39 of the tip electrode 36 fits inside the distal end of the plastic housing 21 and is bonded to the housing by polyurethane glue or the like. The proximal end of the plastic housing 21 is bonded with polyurethane glue or the like to the distal end of the tubing 19 of the tip section 14. It is understood that the tip electrode alternatively may be connected directly to the tubing 19 of the catheter tip section 14 as desired as is well known in the art.

In the embodiment shown, a ring electrode 38 is mounted on the distal end of the plastic housing 21. The ring electrode 38 is slid over the plastic housing 21 and fixed in place by glue or the like. If desired, additional ring electrodes may be used and can be positioned over the plastic housing 21 or over the flexible tubing 19 of the tip section 14.

A temperature sensing means is provided for the tip electrode 36 and, if desired, the ring electrode 38. Any conventional temperature sensing means, e.g., a thermocouple or thermistor, may be used. A preferred temperature sensing means for the tip electrode 36 comprises a thermocouple formed by an enameled wire pair. One wire of the wire pair is a copper wire 41, e.g., a number 40 copper wire. The other wire of the wire pair is a constantan wire 45. The wires 41 and 45 of the wire pair are electrically isolated from each other except at their distal ends where they are twisted together, covered with a short piece of plastic tubing 53, e.g., polyimide, and covered with epoxy. The plastic tubing 53 is then attached in the second blind hole 33 of the tip electrode 36, by polyurethane glue or the like. Alternatively, the wires 41 and 45 can be soldered into the second blind hole 33.

The wires 41 and 45 extend through the second lumen 32 in the tip section 14 and 20 through the central lumen 18 of the catheter body 12. The wires 41 and 45 then extend out through the control handle 16 and to a connector (not shown) connectable to a temperature monitor (not shown).

The tip electrode 36 and ring electrode 38 are each connected to a separate lead wire 40. The lead wires 40 extend through the second lumen 32 of tip section 14, the catheter body 12, and the control handle 16, and each terminate at its proximal end in an input jack (not shown) that may be plugged into an appropriate monitor (not shown). If desired, the portion of the lead wires 40 extending through the catheter body 12, control handle 16 and proximal end of the tip section 14 may be enclosed or bundled within a protective tube or sheath (not shown).

The lead wire 40 for the tip electrode 36 is anchored in the first blind hole 31 of the tip electrode by solder or the like. Any other means for anchoring the lead wire in the tip electrode may also be used. Alternatively, the copper wire 41 of the thermocouple can be used as a lead wire for the tip electrode 36.

A lead wire 40 is attached to the ring electrode 38 by any conventional technique. Connection of a lead wire 40 to the ring electrode 38 is preferably accomplished by first making a small hole through the plastic housing 21. Such a hole can be created, for example, by inserting a needle through the plastic housing 21 and heating the needle sufficiently to form a permanent hole. A lead wire 40 is then drawn through the hole by using a microhook or the like. The ends of the lead wire 40 are then stripped of any coating and soldered or welded to the underside of the ring electrode 38, which is then slid into position over the hole and fixed in place with polyurethane glue or the like.

A preferred means for attaching the catheter body 12 to the tip section 14 is illustrated in FIG. 2. The distal end of the catheter body 12 abuts against the proximal end of the tip section 14 and is attached thereto by polyurethane glue or the like. In the arrangement shown, the proximal end of the tip section comprises a hollowed region 24 into which the distal end of the stiffening tube 20 extends. This design provides better rollover, i.e., allows for bending of the tip section without kinking. Specifically, the stiffening tube 20 provides a transition in flexibility at the junction of the catheter body 12 and more flexible tip section 14, allowing this junction to bend smoothly without folding or kinking, particularly in combination with a tip section having varying stiffness.

A puller wire 42 is provided within the catheter for deflecting the tip section 14. The puller wire 42 is anchored at its proximal end to the control handle 16 and anchored at its distal end to the tip section 14. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

A compression coil 44 is situated with the catheter body 12 in surrounding relation to the puller wire 42. The compression coil extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along its length, the outer surface of the compression coil 44 is covered by a flexible, non-conductive sheath 26 to prevent contact between the compression coil 44 and the lead wires 40 within the catheter body 12. A non-conductive sheath 26 made of polyimide tubing is presently preferred.

The compression coil 44 is anchored at its proximal end to the proximal end of the stiffening tube 20 in the catheter body 12 by glue joint 50 and at its distal end to the tip section 14 by glue joint 51. Both glue joints 50 and 51 preferably comprise polyurethane glue or the like. The glue may be applied by means of a syringe or the like through a hole made between the outer surface of the catheter body 12 and the single lumen 18. Such a hole may be formed, for example, by a needle or the like that punctures the wall of the catheter body 12 and the stiffening tube 20 which is heated sufficiently to form a permanent hole. The glue is then introduced through the hole to the outer surface of the compression coil 44 and wicks around the outer circumference to form a glue joint about the entire circumference of the compression coil.

The puller wire 42 extends into the first lumen 30 of the tip section 14. The puller wire 42 is anchored in the first blind hole 31 of the tip electrode 36. Preferably, a ferrule 43, made of stainless steel or the like, is crimped onto the distal end of the puller wire 42 to add thickness to the puller wire. The ferrule 43 is then attached to the inside of the first blind hole 31 of the tip electrode 36 with solder or the like. Alternatively, the puller wire 42 can be anchored to the side of the tip section 14. Within the tip section 14, the puller wire 42 extends through into a plastic, preferably Teflon®, sheath 81, which prevents the puller wire 42 from cutting into the wall of the tip section 14 when the tip section is deflected.

An electromagnetic sensor 72 is contained within the distal end of the tip section 14. The electromagnetic sensor 72 is located within the plastic housing 21. The distal end of the electromagnetic sensor 72 extends into the third blind hole 35 in the tip electrode 36 and its proximal end extends into the tubing 19 of the tip section 14. The electromagnetic sensor 72 is fixed in the third blind hole 35 by polyurethane glue or the like. If desired, the third blind hole 35 in the tip electrode 36 may be deeper so that the entire electromagnetic sensor 72 is located within the third blind hole 35. Alternatively, the electromagnetic sensor 72 may be mounted proximal to the tip electrode 36. In another alternative embodiment (not shown), the tip electrode 36 has a hollow stem 39 and the electromagnetic sensor 72 is mounted, at least partially, within the hollow stem.

The electromagnetic sensor 72 is connected to an electromagnetic sensor cable 74, which extends through the third lumen 34 of the tip section 14 through the catheter body 12 and out through control handle 16. The electromagnetic sensor cable 74 comprises multiple wires encased within a plastic covered sheath. In the control handle 16, the sensor cable 74 is connected to a circuit board 64. The circuit board 64 amplifies the signal received from the electromagnetic sensor 72 and transmits it to a computer in a form understandable by the computer. Because the catheter is designed for single use only, the circuit board may contain an EPROM chip which shuts down the circuit board approximately 24 hours after the catheter has been used. This prevents the catheter, or at least the electromagnetic sensor, from being used twice.

Suitable electromagnetic sensors for use with the present invention are described, for example, in U.S. Pat. Nos. 5,558,091, 5,443,489, 5,480,422, 5,546,951, 5,568,809, and 5,391,199 and International Publication No. WO 95/02995, the disclosures of which are incorporated herein by reference. A preferred electromagnetic mapping sensor 72 has a length of from about 6 mm to about 7 mm and a diameter of about 1.3 mm.

The electrode lead wire 40, thermocouple wires 41 and 45, and electromagnetic sensor cable 74 must be allowed some longitudinal movement within the catheter body 12 so that they do not break when the tip section 14 is deflected. To provide for such lengthwise movement, tunnels are provided through the glue joint 50, which fixes the proximal end of the compression coil 44 inside the catheter body 12. The tunnels are formed by transfer tubes 27, preferably made of short segments of polyimide tubing. The transfer tube 27 are each approximately 60 mm long and have outer diameters of about 0.021 inch and inner diameters of about 0.019 inch. The thermocouple wires 41 and 45 and electrode lead wire 40 extend through one transfer tube 27 and the sensor cable 74 extends through a second transfer tube 27.

Figure 6:
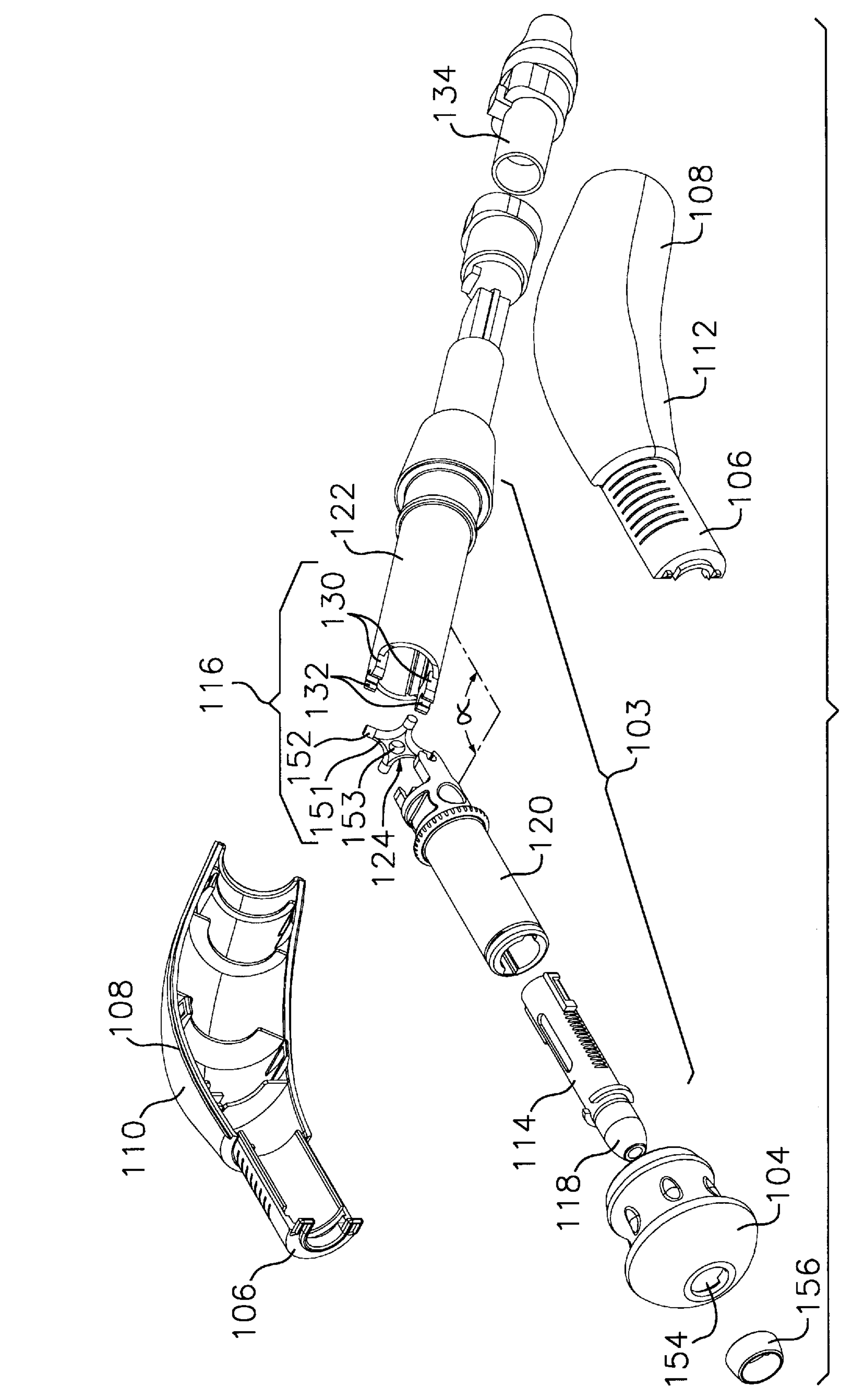
FIG. 6 is a perspective view of the components of a control handle according to the invention.
Figure 7:
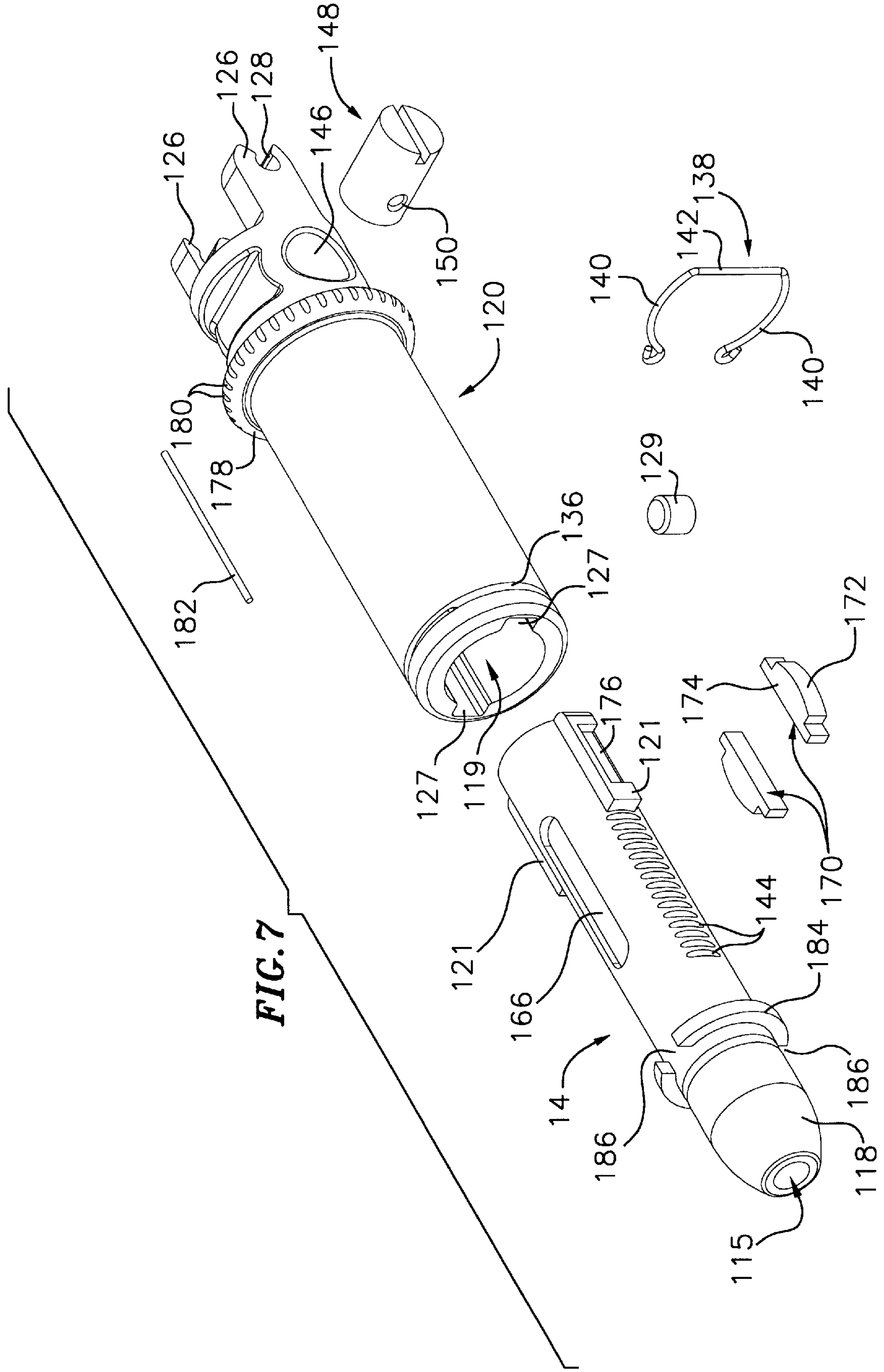
FIG. 7 is an enlarged perspective view of part of the internal assembly of the control handle of FIG. 6.

Longitudinal movement of the puller wire 42 relative to the catheter body 12, which results in deflection of the tip section 12, is accomplished by a suitable manipulation of the control handle 16. As shown in FIGS. 1, 6 and 7, the control handle 16 comprises a housing 102, an internal assembly 103, and a thumb control 104.

The housing 102 is generally curved. More specifically, the housing 102 has a generally cylindrical distal portion 106 and a proximal portion 108 having a rounded bend. The rounded bend of the proximal portion 108 provides improved comfort to the user. The interior of the housing 102 is generally hollow. The housing 102 comprises a first half 110 and a second half 112 that snap together. If desired, the first half 110 and second half 112 of the housing 102 can be assembled together in any other suitable manner, for example, with a press fit or with glue.

The internal assembly 103 comprises a piston 114 and a piston receiving assembly 116. The piston 114 is generally cylindrical and, in the embodiment shown, has a bullet-shaped distal tip 118. The distal tip 118 is fixedly attached to the proximal end of the catheter body 12. The piston 114 contains an internal passage 115 extending therethrough through which the puller wire 42, lead wires 40, thermocouple wires 41 and 45, and sensor cable 74 can pass.

In the depicted embodiment, the piston receiving assembly 116 comprises a distal barrel 120, a proximal barrel 122, and a universal coupling 124. The distal barrel 120 is generally tubular at its distal end forming a piston chamber 119 therein. The piston 114 is longitudinally slidable within the piston chamber 119. The diameter of the piston chamber 119 is slightly greater than the outer diameter of the piston 114.

The distal barrel 120 contains two longitudinal grooves 127. The proximal end of the outer surface of the piston 114 contains two corresponding ribs 121 or other protrusions that fit into the grooves 127 and prevent the piston from rotating relative to the piston receiving assembly 116. As would be recognized by one skilled in the art, other mechanisms for keying the piston 114 to the piston receiving assembly 116 could also be used so that the two members rotate together. For example, protrusions could be provided within the distal barrel, and grooves could be provided on the outer surface of the piston.

Near its distal end, the distal barrel 120 has a circumferential groove 136. Part of the circumferential groove 136 extends through the wall of the distal barrel 120 into the piston chamber 119. A generally horseshoe-shaped clip 138, having two rounded sides 140 and a flat side 142, fits into the circumferential groove 136 so that its flat side 142 extends into the piston chamber 119. The piston 114 has a series of indentations 144 that are aligned with and receive the flat side 142 of the clip 138 when the piston is within the piston chamber 119. When the piston 114 moves distally relative to the piston receiving assembly 116, the interaction of the clip 138 with the indentations 144 provides a clicking mechanism to provide the physician with an indication of how far the piston has been moved.

In the depicted embodiment, the proximal end of the distal barrel 120 is generally open, i.e., has a bore therethrough for passage of the electrode lead wires 40, sensor cable 74, and thermocouple wires 41 and 45, and terminates in two distal prongs 126. Each distal prong 126 contains a generally C-shaped distal notch 128 for receiving the cross bar 124 of the universal coupling, as described further below.

Near the proximal end of the distal barrel 120 is provided a transverse hole 146. An anchor pin 148 extends into the transverse hole 146. The puller wire 42 is anchored to the anchor pin 148 by any suitable mechanism. In a preferred embodiment, the puller wire 42 extends through a hole 150 in the anchor pin 148 and is wrapped around the pin. Because of the bulkiness of the puller wire 42 wrapped around the anchor pin 148, the pin can be wedged into place in the transverse hole 146 without the puller wire coming unwound. If desired, the puller wire 42 can be attached to the anchor pin 148 by glue, solder or the like.

The proximal barrel 122 of the piston receiving assembly is generally tubular to permit the lead wires 40 and sensor cable 74 to pass therethrough. The proximal portion 122 has two proximal prongs 130 at its distal end. Each proximal prong 130 contains a generally C-shaped proximal notch 132 for receiving the cross bar 124 of the universal coupling, as further described below. The proximal end of the proximal barrel 122 terminates in a connector 134 to which the lead wires 40 are connected, and the connector is attachable by means of a cable to a suitable monitor or source of RF energy (not shown). A circuit board (not shown) is mounted in the proximal portion 112. The sensor cable 74 connects to the circuit board, which in turn is electrically connected to a suitable connector.

The cross bar 124 of the universal coupling has four legs 151, each with a generally cylindrical tip 152. Two opposing tips 152 snap into the distal notches 128 of the distal prongs 126 of the distal barrel 120 of the piston receiving assembly 116. The other opposing two tips 152 snap into the proximal notches 132 of the proximal prongs 130 of the proximal barrel 122 of the piston receiving assembly 116. When the piston receiving assembly 116 is assembled, the universal coupling connects the distal barrel 120 to the proximal barrel 122 at an angle a ranging from about 135 to about 180 degrees, preferably about 145 degrees. Accordingly, the piston receiving assembly 116 fits within the housing 102 having a rounded bend. Additionally, when the distal barrel 120 is rotated, the universal coupling permits the proximal barrel 122 to rotate in a corresponding manner. The cross bar 124 has a hole 153 in its center to permit the lead wires 40 and sensor cable 74 to pass therethrough.

When the control handle 16 is assembled, the cylindrical distal portion 106 of the housing 102 extends around the distal end of the distal barrel 120 of the piston receiving assembly 116. The proximal end of the distal barrel 120 along with the universal coupling and proximal barrel 122 of the piston receiving assembly 116 fit within the proximal portion 108 of the housing 102. The piston 114 is slidably disposed within the piston chamber 119 of the distal barrel 120, as described above. The proximal end of the catheter body 12 is fixedly attached to the distal tip 118 of the piston 114 by any suitable mechanism, preferably using a shrink sleeve as is known in the art.

The piston receiving assembly 116 can comprise any other suitable design so that it can slidably receive the piston 114 and rotate with the piston in the curved handle housing 102. For example, the universal coupling, including the cross bar 124 and distal and proximal prongs 126 and 130, can be replaced by another member capable of allowing the distal barrel 120 and proximal barrel 122 to rotate together at an angle, such as a short tightly wound metal coil, similar to the compression coil described above, or a short piece of plastic tubing, similar to that of the catheter body, i.e., having a metal braid therein. The coil or tubing could then be fit over the proximal end of the distal barrel 120 and the distal end of the proximal barrel 122, and glued in place if desired.

In another alternative, both the universal coupling and the proximal barrel 122 could be replaced by a coil or tubing. The coil or tubing is attached to the proximal end of the distal barrel 120. Electrode lead wires 40 and the like are permitted to pass through the coil or tubing to the connector at the distal end of handle.

The thumb control 104 has an internal bore 154 through which the piston 114 extends, with the piston's bullet-shaped distal tip 118 extending out the distal end of the bore. The thumb control 104 is longitudinally held in place over the piston 114 by a ring 156, which preferably snaps over the piston, but can alternatively be held in place by glue or the like.

Deflection of the tip section 14 is affected by distal movement of the thumb control 104 relative to the housing 102 and piston receiving assembly 116. Such movement results in distal movement of the piston 114 and catheter body 12 relative to the piston receiving assembly 116. As discussed above, the puller wire 42 is anchored in the piston receiving assembly 116, and the piston is slidably mounted in the piston receiving assembly. Accordingly, when the catheter body 12 and piston 114 are moved distally relative to the puller wire 42, the tip section 14 is deflected in the direction of the lumen of the tip section into which the puller wire extends.

Rotation of the catheter body 12 is affected by rotation of the thumb control 104 relative to the handle housing 102. The piston 114 is keyed to the thumb control 104 so that rotation of the thumb control results in corresponding rotation of the piston. In the depicted embodiment, the distal end of the piston 114 comprises a distal ring 184 having spaces or breaks 186 on its top and bottom sides. The interior of the thumb control 104 has two protrusions (not shown) that fit into the spaces 186. When the thumb control 104 is assembled over the piston 114, the protrusions mate with the spaces 186 in the distal ring 184 so that rotation of the thumb control correspondingly causes rotation of the piston. Rotation of the piston 114 by rotation of the thumb control 104 causes rotation of the distal portion 120 of the piston receiving assembly 116. As discussed above, the entire piston receiving assembly 116 rotates together due to the universal coupling. Thus, the user can rotate the catheter body 12 without rotating the entire handle 16. In other words, the handle housing 102 can remain stationary when the catheter body 12 is rotated. It is understood that any other suitable means for fixing the thumb control 104 relative to the piston 114 may be used.

As would be recognized to one skilled the art, the thumb control 104 can be any suitable shape. In the depicted embodiment, the thumb control 104 has a circumferential recess 158 between a distal ridge 160 and a proximal ridge 162. The user can move the thumb control 104 distally relative to the housing 102 by pushing on the distal ridge 160. Similarly, the user can move the thumb control 104 proximally relative to the housing 102 by pulling on the proximal ridge 162. By this design, the user can easily and comfortably push and pull the thumb control with one hand. The thumb control 104 further comprises a series of protrusions 164 within the circumferential recess 158 which assist the user in rotating the thumb control.

Additionally, one or more mechanisms can be provided to create friction between the piston 114 and the distal barrel 120 so that, when the piston is moved longitudinally relative to the distal barrel by movement of the thumb control, it does not slide back to its original position when the thumb control is released. One such mechanism comprises a generally oval slot 166 along the length of the piston 114 and a set screw 129 that extends into the slot. The set screw 129 contacts the inner surface of the distal barrel 120 to create friction with the distal barrel. An alternate or additional mechanism comprises two hat-shaped inserts 170, each having a rounded top 172 and a longer flat bottom 174. The inserts 170 are made of a generally flexible or rubbery material, preferably an elastomeric material. The ribs 121 on the piston 114 each contain an indentation 176 into which the flat bottom 174 of each insert fits. The top 172 of each insert 174 contacts the inner surface of the distal barrel 120 to create friction with the distal barrel.

The distal barrel 120 further comprises a textured ring 178 about its circumference. The ring 178 has a number of small grooves 180 about its circumference. A spring 182 is mounted between the housing 102 and distal barrel 120 in generally parallel relation to the distal barrel 120. The spring 182 preferably is a stainless steel wire. As the piston 114 and piston receiving assembly 116 are rotated, the ring 178 rotates in a corresponding manner. The spring 182 is positioned so that it is aligned with the ring 178; as the ring rotates, the spring 182 is positioned within a different groove 180. As the piston receiving assembly 116 and ring 178 are rotated, the contact with the spring 182 creates a clicking sound and feel for the user. Additionally, this design minimizes the tendency of the piston 114 and piston receiving assembly 116 to freewheel backwards when force is built up in the lead wires and sensor cable from the turning of the piston and piston receiving assembly.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A deflectable catheter comprising:

a catheter body having proximal and distal ends and at least one lumen extending therethrough;

a tip section comprising proximal and distal ends and at least one lumen extending therethrough, wherein the proximal end of the tip section is fixedly attached to the distal end of the catheter body;

a control handle comprising:

a housing having a generally hollow interior;

a piston receiving assembly at least partially within the interior of the housing and afforded rotational movement but not longitudinal movement relative to the housing, the assembly comprising a generally tubular member defining a piston chamber;

a piston fixedly attached to the proximal end of the catheter body and extending into the piston chamber of the piston receiving assembly, wherein the piston is afforded longitudinal movement but not rotational movement relative to the piston receiving assembly, whereby rotation of the piston relative to the housing correspondingly rotates the piston receiving assembly, catheter body and tip section;

a puller wire having proximal and distal ends extending from the control handle, through a lumen in the catheter body and into a lumen in the tip section, the proximal end of the puller wire being anchored in the control handle, whereby distal movement of the piston relative to the piston receiving assembly results in distal movement of the catheter body relative to the puller wire; and means for deflecting the tip section in response to distal movement of the catheter body relative to the puller wire.

2. A catheter according to claim 1, wherein the means for deflecting the tip section comprises an off-axis lumen in the tip section into which the puller wire extends and an anchor that anchors the puller wire to the tip section.

3. A catheter according to claim 1, wherein the puller wire is anchored in the piston receiving assembly.

4. A catheter according to claim 1, further comprising a tip electrode.

5. A catheter according to claim 4, wherein the means for deflecting the tip section comprises an off-axis lumen in the tip section into which the puller wire extends and means for fixedly attaching the puller wire to the tip electrode.

6. A catheter according to claim 1, wherein the handle housing is curved.

7. A catheter according to claim 6, wherein the handle housing comprises a generally cylindrical distal portion and a curved proximal portion.

8. A catheter according to claim 6, wherein the piston receiving assembly comprises:

a distal barrel within the handle housing having proximal and distal ends and afforded rotational movement but not longitudinal movement relative to the housing, the distal barrel being generally tubular at its distal end and forming a piston chamber therein; and means for carrying an electrode lead wire from the distal barrel to a connecter at the proximal end of the handle, said means being capable of rotating with the distal barrel.

9. A catheter according to claim 8, wherein the carrying means comprises:

a generally tubular proximal barrel having proximal and distal ends contained at least in part within the handle housing; and a universal coupling connecting the proximal end of the distal barrel to the distal end of the proximal barrel;

whereby rotation of the distal barrel results in corresponding rotation of the proximal barrel.

10. A catheter according to claim 9, wherein the universal coupling connects the distal barrel to the proximal barrel at an angle ranging from about 135 degrees to about 180 degrees.

11. A catheter according to claim 8, wherein the carrying means comprises a coil having proximal and distal ends and contained at least in part within the handle housing, said coil attached at its distal end to the proximal end of the distal barrel.

12. A catheter according to claim to claim 8, wherein the puller wire is anchored in the distal barrel.

13. A catheter according to claim 8, wherein one of the piston and the distal barrel of the piston receiving assembly comprises a protrusion that slidably extends into a longitudinal slot in the other of the piston and distal barrel.

14. A catheter according to claim 8, wherein the piston comprises a protrusion that slidably extends into a longitudinal slot in the distal barrel of the piston receiving assembly.

15. A catheter according to claim 8, wherein the distal barrel of the piston receiving assembly comprises a protrusion that slidably extends into a longitudinal slot in the piston.

16. A catheter according to claim 1, further comprising a thumb control mounted on the piston near its distal end.

17. A catheter according to claim 16, wherein the thumb control comprises a circumferential recess about its midsection formed between a distal ridge and a proximal ridge.

18. A catheter according to claim 17, wherein the thumb control further comprises a series of protrusions within the circumferential recess.

* * * * *